United States Patent
St. George

(12) United States Patent (10) Patent No.: US 9,186,164 B2
St. George (45) Date of Patent: Nov. 17, 2015

(54) IMPACT LITHOTRIPSY TIP

(71) Applicant: Gyrus ACMI, Inc., Southborough, MA (US)

(72) Inventor: Lawrence J. St. George, Sudbury, MA (US)

(73) Assignee: Gyrus ACMI, Inc., Southborough, MA (US)

( * ) Notice: Subject to any disclaimer, the term of this patent is extended or adjusted under 35 U.S.C. 154(b) by 296 days.

(21) Appl. No.: 13/815,628

(22) Filed: Mar. 13, 2013

(65) Prior Publication Data

US 2014/0121673 A1 May 1, 2014

Related U.S. Application Data

(60) Provisional application No. 61/795,807, filed on Oct. 25, 2012.

(51) Int. Cl.
*A61B 17/22* (2006.01)
*A61B 17/221* (2006.01)

(52) U.S. Cl.
CPC .......... *A61B 17/22012* (2013.01); *A61B 17/221* (2013.01); *A61B 2017/22015* (2013.01)

(58) Field of Classification Search
CPC ........... A61B 17/221; A61B 17/22012; A61B 2017/22015
See application file for complete search history.

(56) References Cited

U.S. PATENT DOCUMENTS

| | | |
|---|---|---|
| 3,823,717 A | 7/1974 | Pohlman et al. |
| 3,896,811 A | 7/1975 | Storz |
| 4,154,242 A | 5/1979 | Termanini |
| 4,611,594 A * | 9/1986 | Grayhack et al. ............. 606/127 |
| 4,823,793 A * | 4/1989 | Angulo et al. ................ 606/128 |
| 4,989,583 A | 2/1991 | Hood |
| 4,989,588 A | 2/1991 | Kubota et al. |
| 5,152,768 A | 10/1992 | Bhata |
| 5,246,447 A | 9/1993 | Rosen et al. |
| 5,425,735 A | 6/1995 | Rosen et al. |
| 5,722,980 A | 3/1998 | Schulz et al. |
| 6,183,482 B1 | 2/2001 | Bates et al. |
| 6,224,612 B1 * | 5/2001 | Bates et al. .................... 606/114 |
| 6,676,668 B2 | 1/2004 | Mercereau et al. |
| 6,689,087 B2 | 2/2004 | Pal et al. |
| 6,752,801 B2 | 6/2004 | Engel |
| 7,682,366 B2 | 3/2010 | Sakural et al. |
| 7,942,809 B2 | 5/2011 | Leban |
| 7,993,329 B2 | 8/2011 | Howell et al. |
| 8,007,502 B2 | 8/2011 | Chu et al. |
| 8,092,469 B2 | 1/2012 | Kessler et al. |
| 8,118,823 B2 | 2/2012 | Cotter |

(Continued)

FOREIGN PATENT DOCUMENTS

EP 2219534 9/2011

*Primary Examiner* — Gregory Anderson
*Assistant Examiner* — Son Dang
(74) *Attorney, Agent, or Firm* — Gyrus ACMI, Inc.

(57) ABSTRACT

An apparatus and method are presented comprising a stone retrieval device insertable through a proximal end of a working channel of an endoscope to retrieve a stone at a distal end of an endoscope shaft, and a lithotripsy shaft with a distal tip including one or more guide features to accommodate passage there through of the stone retrieval device and insertable through the proximal end of the working channel of the endoscope, wherein the stone retrieval device extends from the distal end of the endoscope shaft through the lithotripsy shaft.

12 Claims, 5 Drawing Sheets

(56) References Cited

U.S. PATENT DOCUMENTS

| | | |
|---|---|---|
| 8,162,966 B2 | 4/2012 | Connor |
| 2002/0165558 A1 | 11/2002 | Engel |
| 2004/0138677 A1* | 7/2004 | Little et al. .................. 606/127 |
| 2005/0038412 A1 | 2/2005 | Rabiner et al. |
| 2005/0119668 A1* | 6/2005 | Teague et al. ................. 606/127 |
| 2006/0116693 A1* | 6/2006 | Weisenburgh et al. ....... 606/128 |
| 2009/0082780 A1* | 3/2009 | Lu et al. ........................ 606/127 |
| 2010/0286709 A1* | 11/2010 | Diamant et al. .............. 606/128 |

\* cited by examiner

IMPACT LITHOTRIPSY TIP

CROSS REFERENCE TO RELATED APPLICATIONS

This application claims priority to and the benefit of U.S. provisional patent application Ser. No. 61/795,807 filed on Oct. 25, 2012 by Lawrence J. St. George entitled "IMPACT LITHOTRIPSY TIP," the entire disclosure of which is hereby incorporated by reference as if set forth in its entirety for all purposes.

FIELD OF THE INVENTION

The present invention relates to an article and method for breaking physiologic calculi or "stones" using lithotripsy, more particularly to an apparatus and method for breaking stones using a flexible endoscope including a lithotripsy shaft provided with guide features to accommodate passage of a stone retrieval device there through.

BACKGROUND

Medical endoscopes were first developed in the early 1800s and have been used to inspect inside the body. A typical endoscope consists of a distal end comprising an optical or electronic imaging system and a proximal end with controls for manipulating the tools and devices for viewing the image, with a solid or tubular elongate shaft connecting the ends. Some endoscopes allow a physician to pass tools or treatments down a hollow channel, for example, to resect tissue or retrieve objects.

Over the past several decades, several advances have been made in the field of endoscopy, and in particular relating to the breaking up of physiologic calculi in the bile ducts, urinary tract, kidneys, and gall bladder. Physiological calculi in these regions may block ducts and cause a patient a substantial amount of pain and therefore must be broken down and/or removed. Different techniques have been developed to break up stones, including ultrasonic lithotripsy, pneumatic lithotripsy, electro-hydraulic lithotripsy (EHL), and dissolution of calculi using green light, YAG, or holmium lasers.

A number of rigid solid or tubular shaft-based lithotripsy devices that use ultrasonic or pneumatic energy to break the stone into smaller pieces for easier removal from the patient's urologic system have been developed. For example, the Olympus LUS-2, the Gyms ACMI Cyberwand, and the Swiss Lithoclast are such devices. Ultrasonic or acoustic frequency energy is transmitted down a stiff metal shaft and delivered by contact to a kidney stone. Ultrasonic lithotripters require tuned shafts and the effectiveness of these lithotripters depend on their ability to maintain resonance down the length of the shaft (i.e. ultrasonic energy does not travel well around bends or turns). Probe bending can dissipate enough heat to seriously damage adjacent tissue, in addition to the loss of energy transfer at the tip of the probe.

For procedures performed with a tubular shaft device, suction of liquid and debris during the lithotripsy procedure is possible via the center of the tubular shaft. Some devices incorporate and deliver a lower frequency energy component to the kidney stone either through the same shaft or via a second shaft; this second shaft is usually coaxial to the ultrasonic energy shaft (i.e. the Cyberwand). This secondary, lower frequency shows evidence of improving the stone breaking efficiency over a solely ultrasonic energy approach.

The use of such a lithotripsy device requires that the stone being broken is pressed up against some surface, usually an inner wall of the kidney, in order that the vibrational energy can be sufficiently delivered to the stone surface to break it up. Some devices now on the market offer a combination of a lithotripsy shaft and a stone basket (i.e. the Swiss Lithobasket) where the lithotripsy shaft is incorporated into the center of the lithotripsy basket shaft and emerges into the center of the lithotripsy basket. The Swiss Lithobasket allows for the ability to apply the Swiss Lithoclast pneumatically driven shaft to a kidney stone contained in the associated basket, however this device is limited in that no suction is possible through the lithotripsy shaft.

Laser lithotripsy involves the use of laser fibers to effectively break up stones in virtually any area of the urinary system. When used with flexible ureteroscopes, laser fibers can bend around corners and access kidney stones in the lower pole of the kidney. A problem with this approach is that laser fibers have been known to break inside the working channel and damage flexible ureteroscopes. Some techniques have been developed for laser lithotripsy using semi-rigid ureteroscopes to make stones accessible by a straighter path, However, laser lithotripsy in general has a much more expensive start-up cost vs. ultrasonic lithotripsy due to the relative capital equipment costs.

The size, stiffness and length of the straight shafts in much of the existing ultrasonic lithotripter technology only allow for the use of such lithotripters with large shafts in percutaneous procedures, i.e. direct access to stones in the kidney through a small incision in the patient's back and on into the kidney itself. Percutaneous access to physiological calculi with laser lithotripsy provides one solution to prevent breaking and damage of flexible endoscopes during laser or ultrasonic lithotripsy. However, this approach requires more intensive anesthesia and can have longer recovery times for the patient.

Electrohydraulic Lithotripsy (EHL) provides a similar ease of access via a flexible endoscope as laser lithotripsy with generally lower cost, but with also generally lower stone fragmentation efficiency as well as some concerns about local shockwave effects on nearby tissue.

A predominant majority of current lithotripsy shafts are distally terminated smoothly and perpendicular to the shaft axis. This smooth, flat surface, while providing more protection to soft tissue because of the inherent smoothness, can make it extremely easy for the activated shaft to slip off a stone, or for a stone to slide out from beneath the vibrating smooth tip and thus prolong the stone breaking procedure as the physician "chases" the stone around.

Despite the approaches discussed above, there is still a need for an endoscope device that provides a lithotripsy shaft with guide features which can facilitate the passage there through of a stone retrieval device for the capture, retrieval, and disintegration of physiologic calculi. Providing a lithotripsy shaft with guide features would encourage stone fragmentation, being provided with sharp points or edges to more easily stay engaged with a stone and discouraging movement away from the activated tip. A wedged design may more easily force separation of a stone into disparate pieces that can be individually removed or pass on their own.

SUMMARY OF THE INVENTION

The present invention meets one or more of the above needs by providing an endoscope with a lithotripsy shaft with one or more guide features at the distal tip to allow for easy entry and exit of a stone retrieval device into the lithotripsy shaft. The tip of the lithotripsy shaft may be provided with contouring features including tapering or beveling to further assist in a smooth entry of the wires of the stone retrieval device into the lithotripsy shaft. Further, the tip of the lithotripsy shaft may be sharp, pointed, or otherwise piercing in order to maintain contact with a stone during active destruction of physiologic calculi and to aid in advantageous fragmentation of a stone.

Physiologic calculi of interest for these purposes can be found typically in the bile ducts, urinary tract, kidneys, bladder, and gall bladder. Endoscopes to access these stones are referred to as choledochoscopes, ureteroscopes, nephroscopes, cystoscopes, and duodenoscopes respectively. It is contemplated that the details of the present invention may be applied to any type of endoscope.

As an example, in the case of ureteral endoscope access into a kidney, the device of the present invention is capable of retrieving stones in the lower pole or one of the lower calyxes of the kidney and moving them into the upper pole or into the ureteropelvic junction (UPJ) in the urinary system which would provide an access geometry to the captured stone that was a straight or substantially straight line to the kidney using a deflectable distal end of an endoscope tip and then, with the kidney stones more accessible via a substantially straight or minimally curved line path, engage in lithotripsy activities using semi-rigid, rigid or semi-flexible lithotripsy shafts, which are known to be more durable than substantially flexible shaft distal tips. Accordingly, it is contemplated that the apparatus of the present invention would be capable of retrieving and relocating physiologic calculi in any hard to reach position within a patient's anatomy.

In one exemplary embodiment, a stone basket or stone grasper extended from the distal tip of a flexible shaft can access a stone in a traditionally difficult-to-reach location. It is contemplated that this could be accomplished by changing the orientation of a flexible distal end of an endoscope while actively visualizing the anatomy and stone position to retrieve a stone that would be hard to effectively break in the original position in which it was located. The stone may be subsequently pulled into a position which is more easily accessed with a straight, semi-rigid or semi-flexible shaft lithotripter (i.e. at the end of the substantially straight or minimally curved shaft of the endoscope, with the deflection portion of the flexible shaft straightened into a substantially straight or minimally curved line orientation). To accomplish this, the stone retrieval device exits the distal end of the endoscope shaft through a tip of a straight shaft lithotripsy probe, where the lithotripsy probe may be in a retracted position which is behind a substantially deflectable portion of a flexible shaft endoscope, and which may be provided with a wire guide, and then the stone retrieval device is used to grasp and relocate a stone originally found not in a substantially straight-line location for uretural access, to such a substantially straight-line location, for example. Subsequently, the stone retrieval device (i.e. stone basket or stone grasper or other equivalent) may be withdrawn into the endoscope shaft and into the straight lithotripsy shaft. The lithotripsy shaft, which may be driven pneumatically, ultrasonically, mechanically, electromechanically, electromagnetically, or by a combination of different driving power, can then be advanced to crush the stone when the target stone is placed in front of the lithotripsy shaft distal tip. Remaining stone fragments can be retrieved with the stone basket or stone grasper and placed in line with the endoscope shaft to be further broken down.

Accordingly, pursuant to one aspect of the present invention, there is contemplated an apparatus, comprising a stone retrieval device insertable through a proximal end of a working channel of an endoscope to retrieve a stone at a distal end of an endoscope shaft; and a lithotripsy shaft with a distal tip including one or more guide features to accommodate passage there through of the stone retrieval device and insertable through the proximal end of the working channel of the endoscope; wherein the stone retrieval device extends from the distal end of the endoscope shaft through the lithotripsy shaft.

The invention may be further characterized by one or any combination of the features described herein, such as the one or more guide features comprise protrusions from the distal tip of the lithotripsy shaft; the protrusions are beveled, tapered, or a combination of both; a distal end of the protrusions is sharp; the lithotripsy shaft is driven pneumatically, ultrasonically, mechanically, electromechanically, electromagnetically, or by a combination of different driving power; the stone retrieval device is a stone grasper; the stone retrieval device is a stone basket; the stone basket is a three wire, four wire, six wire, or eight wire basket; the stone basket is tipless or tipped.

Accordingly, pursuant to another aspect of the present invention, there is contemplated a method, comprising passing a stone retrieval device through one or more guide features of a lithotripsy shaft at a distal tip of a flexible endoscope; retrieving a stone and bringing it substantially in line with a longitudinal axis of the lithotripsy shaft; withdrawing the stone retrieval device through the one or more guide features into the lithotripsy shaft; and driving the lithotripsy shaft under power toward a stone.

Further aspects, advantages and areas of applicability will become apparent from the description provided herein. It should be understood that the description and specific examples are intended for purposes of illustration only and are not intended to limit the scope of the present disclosure.

DESCRIPTION OF THE DRAWINGS

The drawings described herein are for illustration purposes only and are not intended to limit the scope of the present disclosure in any way.

DETAILED DESCRIPTION OF THE INVENTION

Figure 1:
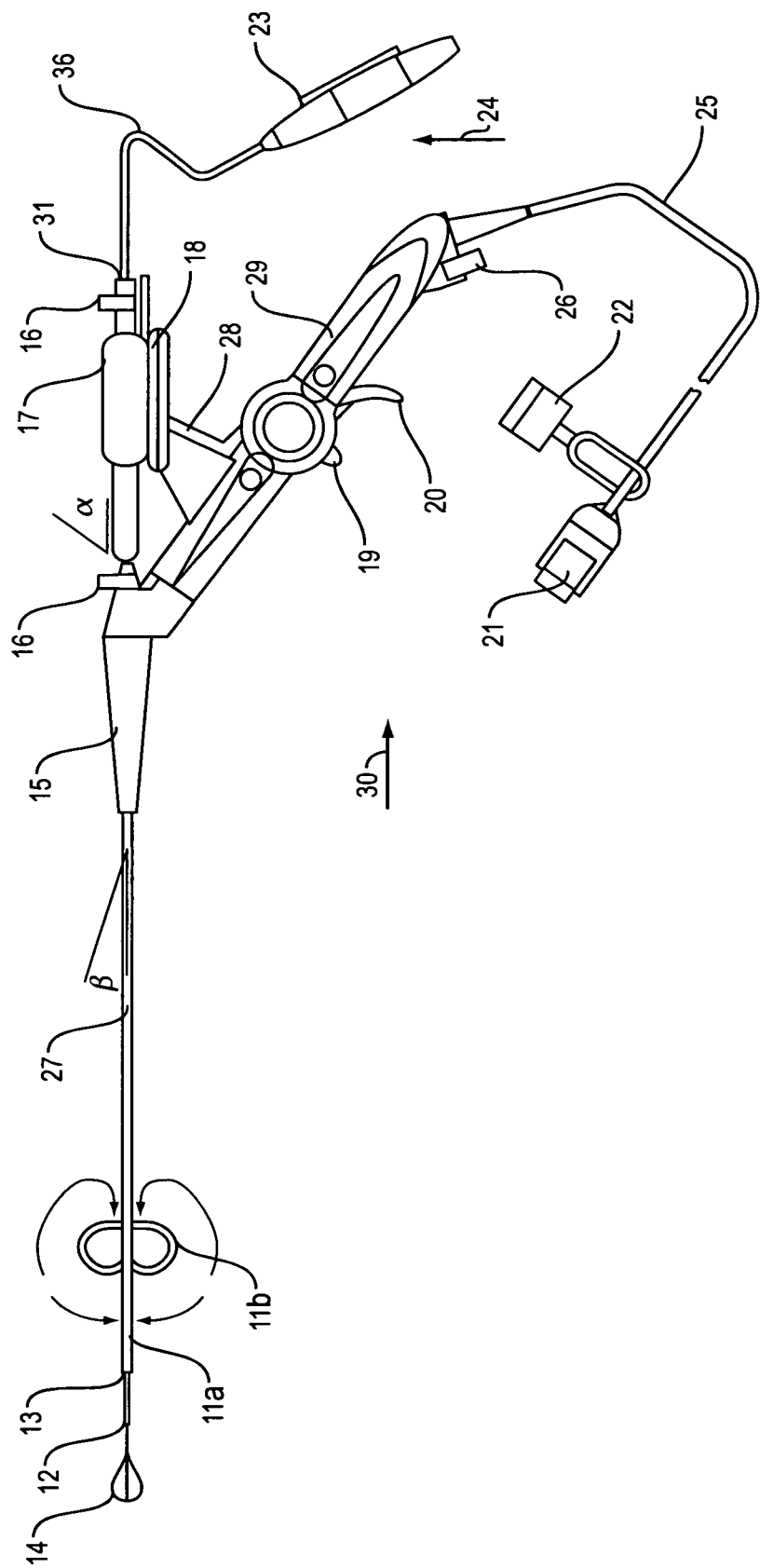
FIG. 1 is a cross-sectional profile view of an illustrative example of an endoscope in accordance with the teachings of the present invention.

The following description is merely exemplary in nature and is not intended to limit the present disclosure, application, or uses.

As will be seen, the devices and methods taught herein offer convenient access with a flexible endoscope to stones in the body. The present invention describes an improved lithotripsy system which is comprised of a flexible endoscope, an impact shaft lithotripter, and a stone retrieval device, which allows for more efficient access to, as well as acquisition and fragmentation of, physiologic calculi.

One embodiment of the invention may use a tubular impact-transmitting lithotripsy shaft provided with guide features at the tip for better, more consistent engagement with a stone for better fragmentation efficiency. Such guide features could also be designed to have better compatibility with stone retrieval device design so as to protect the elements of a stone retrieval device and facilitate the ability of the stone retrieval device to bring a stone to the distal tip of the lithotripsy shaft. Such a lithotripsy shaft may have a substantially stiff characteristic, capable of providing column strength and rigidity, in order to transmit impact energy from its driver to its distal tip and thus may have limited flexing or bending capability while retaining such impact energy transmission capabilities. It is contemplated that such a lithotripsy shaft would preferably be provided access to a stone needing fragmentation via a straight line path, or substantially close to a straight line path. The angle with which the lithotripsy driver may deviate from the lithotripsy shaft is described as angle $\alpha$. The straighter the access from the lithotripsy driver to the lithotripsy shaft, the better suited the device as a whole will be to utilize energies which are more effectively transmitted via a straight shaft, including ultrasonic energy. Furthermore, the angle of deflection that the lithotripsy shaft may deviate from a straight line out from its' exit from the lithotripsy driver to a stone needing fragmentation and this deflection angle may be described as $\beta$. The ability to effectively fragment a stone via a slightly curved shaft is highly desirable as the anatomy encountered may not support an entirely straight access to a stone.

The driver for the lithotripsy shaft may be connected to and/or supported by, or integrated into the design of the endoscope in order to provide a more "hands free" configuration. The driver for the lithotripsy shaft could be connected to the flexible endoscope in such a way that it is mounted on a sliding translation stage or mechanism which would facilitate a more automatic positioning of the lithotripsy shaft relative to the deflection section of the flexible endoscope. When moved to the proximal/rear end of the sliding mechanism, the driver and the lithotripsy shaft would be pulled back to a position where the lithotripsy shaft was removed from the deflection section of the flexible endoscope in such a way that the deflection section of the flexible endoscope would be able to perform its full deflection function without interference from the lithotripsy shaft. When moved distal/forward position of the sliding mechanism, the lithotripsy shaft would, through a straight flexible endoscope shaft, be moved forward through the working channel and the distal tip of the lithotripsy shaft would exit the working channel and ideally be positioned at an optimum distance from the front of the flexible endoscope tip for visualization and stone fragmentation activity. Furthermore, it may be advantageous to have a user-controlled moving lever positioned for easy activation that, when activated, would provide to the user an ability to move the distal tip of the lithotripsy shaft distally and proximally a small distance and thus have better control over how the lithotripsy shaft engages the stone, perhaps without having to move the entire endoscope forwards and backwards in the anatomy of interest. Such a translation mechanism could be utilized to support a holder for other working channel tools, such as a laser fiber, which may also benefit from such translation and fine position control capabilities while providing the user with additional ease of use.

By way of example, when beginning a procedure such as kidney stone removal, one could have a combined assembly that included a flexible endoscope, an attached lithotripsy driver with lithotripsy shaft located in the flexible endoscope working channel, and a stone basket device inserted into this overall assembly and ready for easy deployment to capture a stone for ultimate removal from the urinary system. The stone lithotripsy driver and shaft would be positioned at a retracted position so that the deflection section of the flexible endoscope would not experience limitations in movement range due to interference from the lithotripsy shaft.

It is contemplated that different output accessories can be used with the device of the present invention. In one embodiment, a lithotripsy shaft may be used in combination with a stone retrieval device. Another embodiment might include a laser fiber used in combination with a stone retrieval device. Various other alternatives and configurations are possible to remove a calculus of interest and are herein incorporated by reference.

It is contemplated that at a point where the flexible endoscope is straightened out, the distal tip of the lithotripsy shaft could be advanced forward and out of the tip of the flexible endoscope such that it could come in direct contact with the stone to be fragmented. This could be accomplished either after the stone is released from the stone retrieval device with the stone basket retracted into the endoscope and the stone in an advantageous position for the purposes of fragmentation or with the stone contained in the stone retrieval device and drawn toward the lithotripsy shaft tip by a retraction of the stone retrieval device. Subsequently, the lithotripsy shaft driver may be activated and the kidney stone of interest fragmented. If further stones needed to be fragmented and they were not accessible via a straight path, the lithotripsy shaft could be retracted and the next stone of interest could be accessed, captured, and fragmented in the same way.

With the stones and fragments positioned closer to the exit of the kidney, and the stone basket accessible as part of the overall assembly, the stones or fragments could be captured by the stone retrieval device and withdrawn from the patient, with probably less internal damage to the kidney and ureter as most of the extraction activities would be along a substantially straight line. It is contemplated that the ideas of the present invention would result in less bumping and rubbing against the internal surfaces of the kidney and ureter and less tissue and blood debris generated and thus less compromise of visualization during the course of a procedure.

In one embodiment of the invention, the lithotripsy shaft can be applied to a stone by itself, especially to reduce the size of a larger stone. Subsequently, a stone retrieval device can be deployed through the working channel after the lithotripsy shaft has been removed to acquire and hold a smaller stone or stone fragment for further lithotripsy. It is contemplated that irrigation or evacuation may be applied through the lithotripsy shaft as a tubular center core would allow for sufficient access, in particular for the case where there is no stone basket shaft present within the lithotripsy shaft.

In another embodiment of the invention, a friction adjustment may be provided to set a drag friction in order to prevent the stone retrieval device wires from becoming overstressed and breaking. The friction adjustment setting may be modified for different stone retrieval device wire thicknesses and arrangements. Such a friction adjustment would help to ensure that the stone retrieval device wires were not coming into excessive frictional contact with the edges of the lithotripsy shaft and breaking during stone destruction or retrieval. Once the tension in the wires reached the desired limit, the tension on the stone retrieval device would be released or reduced, reducing the friction of that device with the tip of the lithotripsy shaft to prevent breaking of the stone retrieval device wires or filaments.

Turning now to the drawings to illustrate examples of embodiments of the present teachings, FIG. 1 details the lithotripsy system using a flexible endoscope of the present invention. Endoscope 30 is provided with flexible shaft 27, mount 28, lithotripsy shaft 12, stone retrieval device 14, translation stage 18, lithotripsy driver 17, as well as control elements 18, 19, 20, and 23.

Flexible Shaft

Functionally, flexible shaft 27 is capable of active deflection at a distal tip 13 in order to reach around corners and bring stones to locations that allow for improved straight line access such that lithotripsy activities will be more effective.

Flexible shaft 27 enters the body in an extended position 11a, and once within the anatomy of interest can manipulate and deflect to deflected position 11b using control wires. Control wires may be activated and manipulated using deflection control lever 19. Deflection control lever may be capable of being locked in the center (i.e. in order to pull difficult to reach stones into a position substantially in front of the straight end of the distal tip 13 of endoscope 30).

Handle

Functionally, handle 29 may be connected to a proximal end of the flexible shaft via a strain relief 15 and may be oriented at an angle with respect to the longitudinal axis of the straight portion of flexible shaft 27. Providing handle 29 at an off-axis angle allows for substantially improved straight line access through working channel 31 for lithotripsy shaft 12 to impart maximum impact to physiologic calculi of interest at the distal end of the device.

One embodiment of the present invention provides lithotripsy driver 17 in a straight line path with the straight portion of flexible shaft 27. Another embodiment provides lithotripsy driver 17 substantially in line with the straight portion of flexible shaft 27 (i.e. lithotripsy driver 17 may be oriented at an angle $\alpha$ with respect to the longitudinal axis of a straight portion of the flexible shaft). Angle $\alpha$ may range from 0±15°, preferably from 0±5°, and more preferably from 0±2°. Angle $\alpha$ may be larger depending on shaft flexibility; however, the straighter the shaft that is provided, the better suited the device as a whole will be to utilize energies which are more effectively transmitted via a straight shaft, including ultrasonic energy.

Rigid or semi-rigid lithotripsy shafts 12 may enter through working channel 31 and effectively break up physiologic calculi with these specifications. Strain relief 15 is provided to protect the base of the shaft where it is attached to the scope from excessive bending at the proximal end of the shaft. The angle of deflection that the lithotripsy shaft may deviate from a straight line out from the lithotripsy driver to a stone needing fragmentation is described as angle $\beta$. The ability to effectively fragment a stone even via a slightly curved shaft is highly desirable as the anatomy encountered may not support a totally straight access to a stone. Angle $\beta$ may range from 0±15°, preferably from 0±5, and more preferably from 0±2°. Angle $\beta$ may be larger depending on lithotripsy shaft flexibility; however, the straighter the lithotripsy shaft that is provided, the better suited the device as a whole will be to utilize energies which are more effectively transmitted via a straight lithotripsy shaft, including ultrasonic energy.

Mounting Platform

A mounting platform 28 may be mounted to a top portion of handle 29 in a generally perpendicular orientation with respect to handle 29 in order to provide stability for lithotripsy driver 17 and translation stage 18 at their connection to strain relief 15. The functionality of such a platform or other mechanism for locating a lithotripsy or other kind of driver mechanism, that is, to hold, align, and longitudinally translate a lithotripsy driver or other useful mechanism substantially in-line with the axis of the shaft of the endoscope may be realized by different configurations than is presented herein. The platform may be taken to mean another mechanism for supporting a driver, for lithotripsy or otherwise, or a holding mechanism for supporting the passage of an elongate device down the working channel of the endoscope.

Stone Retrieval Device

Stone retrieval device 14, which may be a stone basket or stone grasper, may be insertable into the proximal end of endoscope 30 through working channel 31 for retrieval of a stone at a distal end of the flexible shaft 27 of the endoscope by protruding therefrom. Stone retrieval device 14 may consist of any number of wires or filaments, but typically would have three, four, six, or eight wires or filaments, and may either be provided with a tip or be tipless at a distal end.

Lithotripsy Shaft

Figure 2:
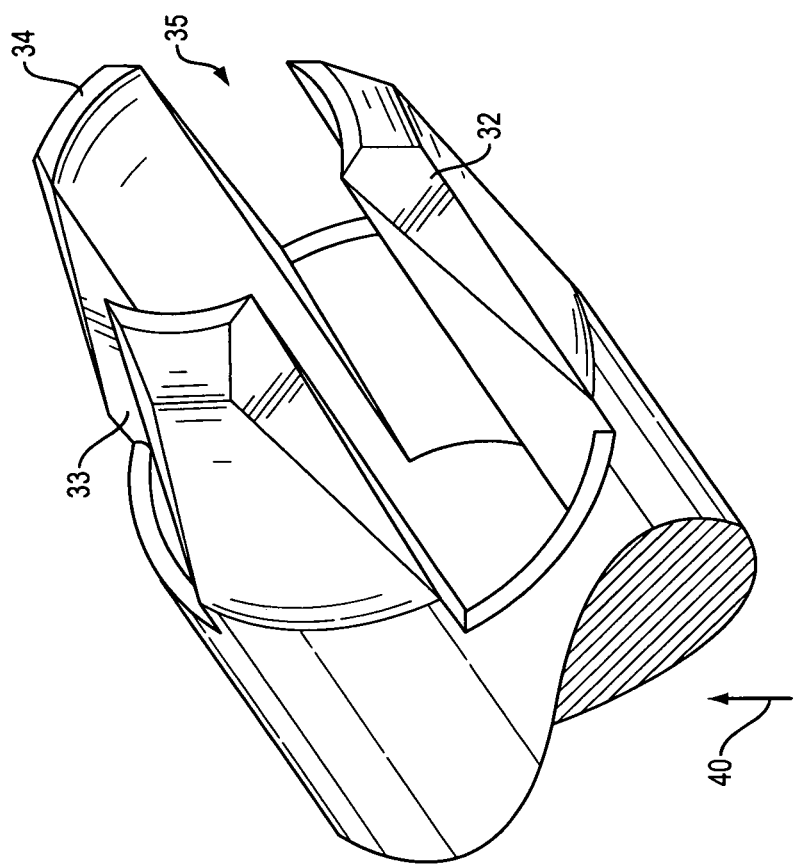
FIG. 2 is an exploded view of a lithotripsy shaft tip with guide features in accordance with one embodiment of the present invention.
Figure 4:
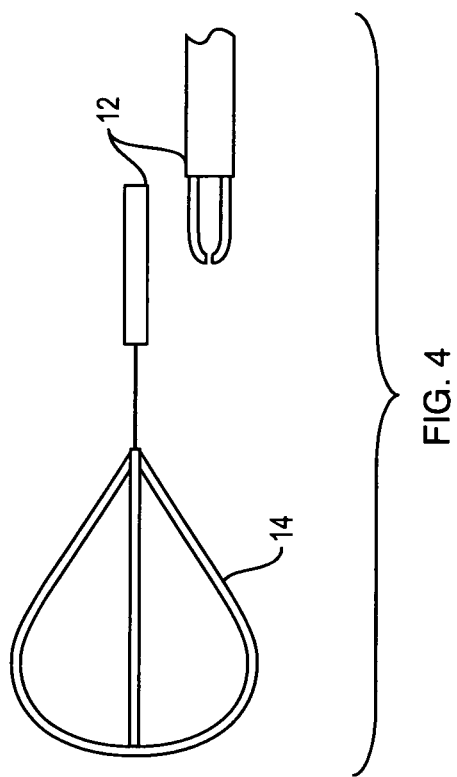
FIG. 4 is a cross-sectional profile view of an illustrative example of a lithotripsy shaft tip with guide features and a stone retrieval device in accordance with the teachings of the present invention.
Figure 3:
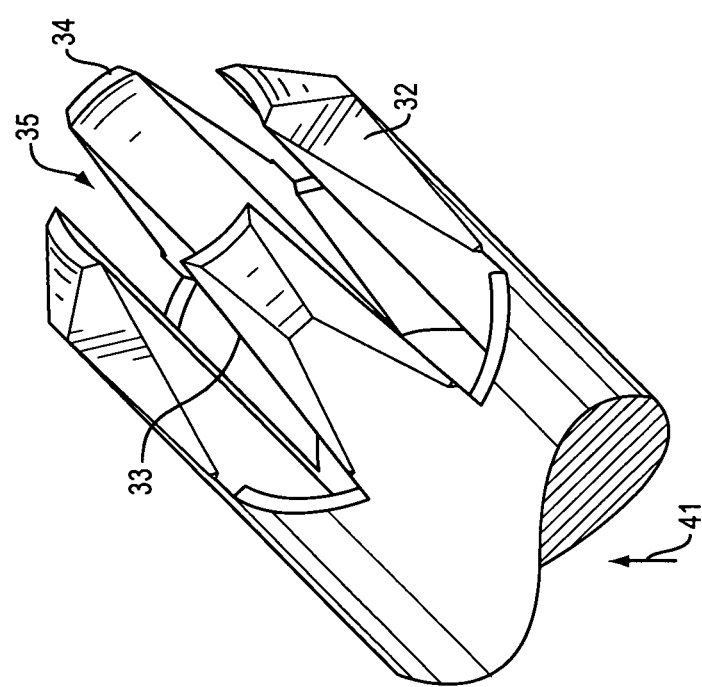
FIG. 3 is an exploded view of a lithotripsy shaft tip with guide features in accordance with another embodiment of the present invention.

Lithotripsy shaft 12 including one or more guide features at a distal end of the lithotripsy shaft to facilitate passage of wires of the stone retrieval device there through. Guide features may include, as illustrated in FIGS. 2 and 3 beveling 32, tapering or funnel-shaping 33, protrusions 34, guide passages 35, and/or sharp or pointed tips. In the illustrated embodiment, the distal tip of lithotripsy shaft 12 is provided, with either three or four protrusions. It is contemplated that these features may better protect the basket wires and guide their exit from the center of the hollow lithotripsy shaft. FIG. 4 illustrates a close-up view of the stone retrieval device 14 extended through the guide features at the distal end of lithotripsy shaft 12.

Specific shaping of the lithotripsy shaft tip may encourage stone fragmentation by relatively sharp points or edges to more easily stay engaged with a stone and discourage movement away from the activated tip, and perhaps a wedged design to more easily force separation of a stone into disparate pieces.

The advantage of having "points" or pronounced edges at the tip is that these would either "dig into" a kidney stone or at least align with an existing rough texture on a harder stone and thus the stone and shaft would be "interlocked" as the shaft was pushed against the stone and activated. Stone breaking efficiency would be higher and thus procedures would be shorter and more effective as the physician would spend less time "chasing" a stone around than they might with a smooth distal tip on the lithotripsy shaft.

The shape of the tip can also be designed to be compatible with different designs of stone baskets, which can be inserted through the core of the shaft and used to capture and hold a kidney stone for lithotripsy by the shaft. Such designs as would be compatible with stone baskets would be likely better described as crenellated as there would clearly be slots that the stone basket wires or elements would naturally slip into and be more protected therein, i.e. not compressed between the stone material and the vibrating metal tip and therefore at risk to be cut between the two.

Three-point distal tip 40 of lithotripsy shaft 12 may easily facilitate passage of stone retrieval devices with either three or six wires (i.e. three-point symmetry). Four-point distal tip 41 of lithotripsy shaft 12 may easily facilitate passage of stone retrieval devices with either four or eight wires (i.e. four-point symmetry). Guide passages 35 in either case provide easy passage of wires there through. Beveling and tapering further facilitate passage of stone retrieval device wires with minimal friction and/or abrasion. The above mentioned features further minimize force and stress to the wires while the stones are being broken up, and it is contemplated that such features would contribute to longer stone retrieval device lifetimes.

In one embodiment of the invention, the lithotripsy shaft may be cut in special patterns along its length, such as with a laser, to make it more flexible yet maintain the column strength necessary to deliver sufficient ultrasonic or acoustic frequency or impact energy, for example, to a kidney stone to break it up. Such shaft modifications would make it easier to deliver the lithotripsy energy higher in the ureter and into the mid or upper poles of the kidney.

The lithotripsy shaft may be fabricated in part, large or small, or entirely, of a closed coil spring, of round or flat wire or some variation in between, to have more flexibility and ability in transmitting the stone breaking kinetic energy along a curved or non-straight path. The lithotripsy shaft may be comprised of other materials, including shape memory alloys, including Nitinol and Tinel, titanium, stainless steel, or other materials known in the art. The shape memory alloy material is used for its superelastic properties exhibited by the material's ability to deflect and resiliently return to its natural or predetermined position even when material strains approach 4%, or an order of magnitude greater than the typical yield strain of 0.4% giving rise to plastic deformation in common metals. Thus, the term "superelastic alloy" is used to denote this type of material. The distal tip of the lithotripsy shaft may be of a different material than that of the shaft, or have different treatment, such as localized hardening, than the rest of the shaft so as to be more durable against hard stone material. The distal tip may be smaller, or larger, in diameter than the lithotripsy shaft, in order to gain better access to a stone, or have a better stone breaking capability. For example, a larger tip on a smaller shaft would have more potential area of contact on a stone for better stone breaking capability while allowing for better shaft flexibility and/or irrigation capacity.

Different methods may be used to manufacture the guide features of the distal tip of lithotripsy shaft 12. By way of example, one such method is electrical discharge machining (EDM). This method would allow for precise cutting from a blunt end of a lithotripsy shaft to form beveling, tapering, sharp points, and/or protrusions.

Lithotripsy Shaft Driver

Lithotripsy shaft driver 17 may be controlled using various types of driving power, including pneumatic, ultrasonic, mechanical, electromechanical, electromagnetic, hydraulic, piezoelectric, or by a combination of different driving power. In the case of electromagnetic driving power, solenoids or coils, or the like may be used within lithotripsy shaft driver 17 to control the movement of lithotripsy shaft 12. In the case of ultrasonic driving power, the frequency of operation would be greater than 20 kHz in order to reduce the discomfort from excessive audible noise. In the case of electromechanical or pneumatic driving power (i.e. an "impact" driven lithotripsy shaft), the frequency of operation would be typically less than 10-100 Hz. Pneumatic driving power may include the use of $CO_2$ cartridge or a connection to an air supply hose. One example embodiment of mechanical driving force includes use of a spring-loaded cam shaft or mechanism to produce abrupt forward motion and a slower backward motion of the lithotripsy shaft to impart greater impact on the physiologic calculus of interest. In a preferred embodiment, lithotripsy shaft 12 will be driven under ultrasonic power, resulting in more effective stone destruction and shorter procedure duration.

Choice of driving power will affect the strength as well as the frequency of impact, and will therefore affect the speed and effectiveness of calculus disintegration. Smaller stones may require higher oscillation frequencies, while larger stones may require lower oscillation frequencies, for more efficient reduction of stone size. It may be possible to determine, in advance of the procedure, the composition or hardness of the calculi of interest by various imaging techniques, including but not limited to ultrasound, X-ray, CT, or MRI, and thereby tailor the type of driving power to be the most effective technique for a given calculus type. It may be possible to swap out the type of driver during the lithotripsy procedure to more effectively disintegrate a challenging calculus.

Figure 5A:
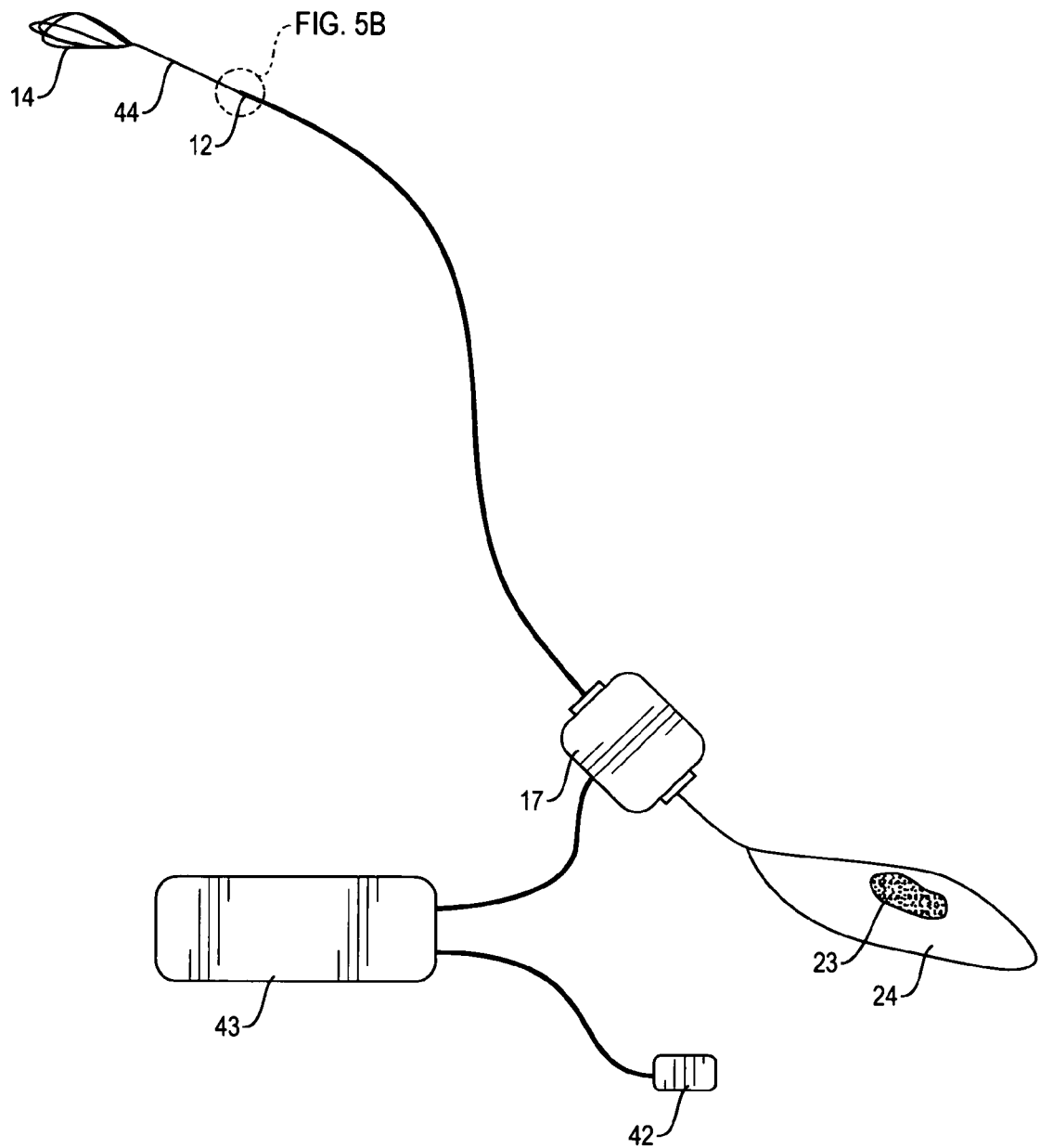
FIG. 5A is a perspective view of one embodiment of the present invention showing the lithotripsy shaft, driving mechanism, and stone retrieval device.
Figure 5B:
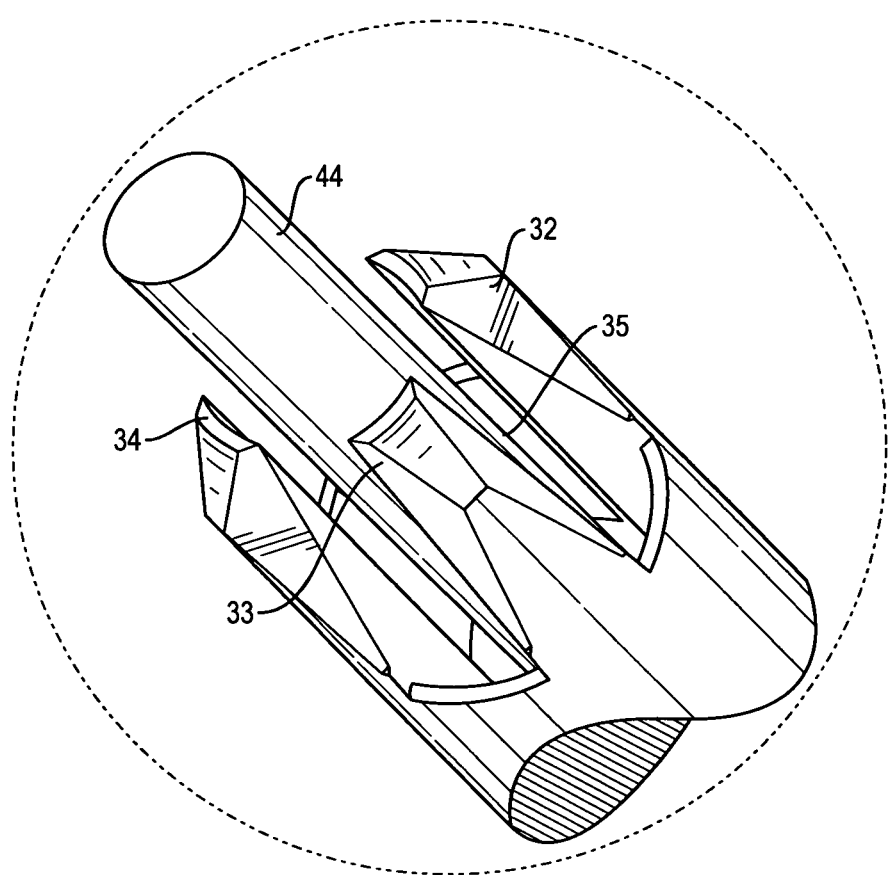
FIG. 5B is an exploded view of the distal end of the lithotripsy shaft with stone retrieval device extending therethrough in accordance with the teachings of the present invention.

FIG. 5A details an embodiment of the present invention which is capable of operation with or without the use of an endoscope, and an associated shaft, handle, and mounting platform. In this embodiment, stone retrieval device 14 can extend beyond the tip of lithotripsy shaft 12, which may be provided with guide features, for retrieval of stones to a more straight line trajectory for the lithotripsy shaft driver to break up physiologic calculi. Lithotripsy shaft driver 17 connects to shaft driver generator 43, which generates the power needed to drive lithotripsy shaft 17. In this illustrated embodiment, footswitch 42 is included for control of shaft driver generator 43. FIG. 5B illustrates the distal end of a lithotripsy shaft 12 with guide features with stone retrieval device extending therethrough at the distal end an insertion device.

Controls

Controls may be provided for controlling movement of any one or more of the following: deflection of the active deflection section of the flexible shaft, extension and retraction of the stone retrieval device, the extension and retraction of the lithotripsy shaft from the distal end of the endoscope, and/or the driving of lithotripsy shaft to impact active force upon a calculus of interest.

Control of deflection of the active deflection section of the flexible shaft 27 may be accomplished through deflection control lever 19. Control wires built into flexible shaft 27 control deflection in a first and second direction via control lever 19. Control lever 19 may be provided with a lock position to restrict the distal end 13 of flexible shaft 27 to an extended and essentially straight line position 11a. Extended position 11a allows for more effective stone breaking by facilitating more of the energy from lithotripsy driver 17 impacting a physiologic calculus of interest.

Control of extension and retraction of the stone retrieval device may be accomplished through stone retrieval device handle 24 and thumb control 23. Thumb control 23 may be in the form of a slider, trigger, thumb wheel, scissors-like handle grip, or other reasonable control mechanism. Thumb control 23 may act to move stone retrieval device into and out of the distal tip of lithotripsy shaft 12 and the distal tip of flexible shaft 27. Movement of the stone retrieval device into the distal tip of lithotripsy shaft 12 causes stone retrieval device 14 to close and, similarly, movement of stone retrieval device out of the distal tip of lithotripsy shaft 12 and the distal tip of flexible shaft 27 causes stone retrieval device 14 to open. Stone retrieval device 14 can be extended and retracted from the distal tip 13 of flexible shaft 27 while distal tip 13 is either fully extended, fully retracted, or at any position there between.

Control of extension and retraction of the lithotripsy shaft 12 from the distal end of the endoscope may be accomplished by different mechanisms. For example, in the illustrated embodiment, control of lithotripsy shaft 12 is accomplished through a combination of translation stage 18 and slide lever control 20. Translation stage 18 allows for movement between one of two positions. A first position being a non-deployed position in which the distal end of lithotripsy shaft 12 is withdrawn such that it does not interfere with active deflection of the distal tip of flexible endoscope into a deflected position such as position 11*b*. A second position being a deployed position in which the lithotripsy shaft is extended beyond the distal tip of flexible shaft 27 by a distance sufficient enough to allow physiologic calculi to be impacted and broken down. Slide lever control 20 may provide fine tuning of the position of the distal tip of lithotripsy shaft 12 toward or away from a target location with more exact precision. In an alternate configuration, a mechanism for advancing and controlling the position of a laser fiber or other filamentous tool may be located in place of the lithotripsy driver, providing more advantageous and fine control over such filamentous tools than can be had by manual manipulation. The translation stage 18 is a representation of one kind of embodiment of a portion of the invention and its' function may be implemented by other configurations such as, for example, a moving cylinder in a tube.

Control of lithotripsy shaft driver 17 may be accomplished via buttons on the proximal end of the endoscope handle 29, through a separate console control, or via a footswitch, for example. Control of lithotripsy shaft driver 17 would function to turn active stone breaking on or off for one or more of the various types of driving techniques described above. Active stone breaking would preferably occur in the present invention when the flexible endoscope shaft was in a substantially extended position, as in position 11*a*, so as to minimize the dissipation of energy around a bend.

The invention claimed is:

1. An apparatus, comprising:
   a stone retrieval device insertable through a proximal end of a working channel of an endoscope to retrieve a stone at a distal end of an endoscope shaft; and
   a lithotripsy shaft with a distal tip including one or more fixed guide features to accommodate passage there through of the stone retrieval device and insertable through the proximal end of the working channel of the endoscope;
   wherein the stone retrieval device extends from the distal end of the endoscope shaft through the lithotripsy shaft,
   wherein the lithotripsy shaft is configured to cause stone destruction.

2. The apparatus of claim 1, wherein the one or more fixed guide features comprise protrusions and the protrusions form a wedge shape.

3. The apparatus of claim 2, wherein a distal end of the protrusions are provided with a slanting edge.

4. The apparatus of claim 2, wherein the lithotripsy shaft is configured to dig into a stone.

5. The apparatus of claim 4, wherein the one or more fixed guide features are configured to protect the basket wires and guide an exit of the basket wires through the protrusions at the distal end of the lithotripsy shaft.

6. The apparatus of claim 5, further comprising a friction adjustment to prevent the basket wires from becoming overstressed.

7. The apparatus of claim 4, wherein the stone basket is tipless.

8. The apparatus of claim 1, wherein the lithotripsy shaft is driven pneumatically, ultrasonically, mechanically, electromechanically, electromagnetically, or by a combination of different driving power.

9. The apparatus of claim 8, wherein the stone retrieval device is a stone grasper or a stone basket.

10. A method, comprising:
    passing a stone retrieval device through one or more guide features of a lithotripsy shaft at a distal tip of a flexible endoscope;
    retrieving a stone and bringing it substantially in line with a longitudinal axis of the lithotripsy shaft;
    withdrawing the stone retrieval device through the one or more guide features into the lithotripsy shaft; and
    driving the lithotripsy shaft under power toward a stone,
    wherein the lithotripsy shaft comes into contact with a stone and breaks up the stone.

11. The method of claim 10, wherein the fixed guide features act as a wire guide.

12. An apparatus, comprising:
    a stone retrieval device insertable through a proximal end of a working channel of an endoscope to retrieve a stone at a distal end of an endoscope shaft; and
    a lithotripsy shaft with a distal tip including one or more fixed guide features to accommodate passage there through of the stone retrieval device and insertable through the proximal end of the working channel of the endoscope,
    wherein the lithotripsy shaft is capable of causing stone destruction,
    wherein the fixed guide features protect the basket wires and guide an exit from a center of the lithotripsy shaft.

* * * * *